(12) United States Patent
Kosasky

(10) Patent No.: US 7,526,945 B1
(45) Date of Patent: May 5, 2009

(54) SYSTEM AND METHOD FOR MEASURING EXTENSIONAL RHEOLOGY OF BODILY FLUIDS

(76) Inventor: Harold J. Kosasky, 225 Woodland Rd., Chestnut Hill, MA (US) 02467

( * ) Notice: Subject to any disclaimer, the term of this patent is extended or adjusted under 35 U.S.C. 154(b) by 0 days.

(21) Appl. No.: 12/165,988

(22) Filed: Jul. 1, 2008

(51) Int. Cl.
*G01N 11/00* (2006.01)
(52) U.S. Cl. .................................................. 73/54.01
(58) Field of Classification Search ................ 73/54.01
See application file for complete search history.

(56) References Cited

U.S. PATENT DOCUMENTS

| | | | |
|---|---|---|---|
| 3,926,037 | A | 12/1975 | Kopito et al. |
| 4,002,056 | A | 1/1977 | Kopito et al. |
| 4,674,322 | A | 6/1987 | Stangeland |
| 4,770,186 | A | 9/1988 | Regas et al. |
| 4,779,627 | A | 10/1988 | Kosasky |
| 4,884,437 | A | 12/1989 | Constant et al. |
| 5,043,888 | A | 8/1991 | Uriarte |
| 5,209,238 | A | 5/1993 | Sundhar |
| 5,572,370 | A | 11/1996 | Cho |
| 5,640,968 | A | 6/1997 | Kosasky |
| 5,788,649 | A | 8/1998 | Kosasky |
| 5,837,197 | A | 11/1998 | Porrazzo et al. |
| 5,851,190 | A | 12/1998 | Kosasky |
| 6,149,591 | A | 11/2000 | Henderson et al. |
| 6,149,604 | A | 11/2000 | Kosasky |
| 6,159,159 | A | 12/2000 | Canter et al. |
| 6,234,974 | B1 | 5/2001 | Catt et al. |
| 6,454,726 | B1 | 9/2002 | Catt et al. |
| 6,468,223 | B2 | 10/2002 | Kaga |
| 6,575,021 | B1 | 6/2003 | Kosasky et al. |
| 6,591,663 | B1 | 7/2003 | Murray et al. |
| 6,793,886 | B1 | 9/2004 | Weissmahr |
| 2004/0171964 | A1 | 9/2004 | Heitz |
| 2005/0165326 | A1 | 7/2005 | Kirsner |
| 2005/0215858 | A1 | 9/2005 | Vail, III |
| 2006/0178638 | A1* | 8/2006 | Reynolds ..................... 604/191 |
| 2006/0178641 | A1* | 8/2006 | Reynolds ..................... 604/218 |
| 2006/0178644 | A1* | 8/2006 | Reynolds ..................... 604/232 |

OTHER PUBLICATIONS

Gohara, K, et al., A new automatic device for measuring the spinnbarkeit of saliva: the Neva Meter, Journal of Dentistry, (2004) pp. 335-338, vol. 32, Elsevier.
Oliveira, Monica S.N., et al, Iterated stretching, extensional rheology and formation of beads-on-a-string structures in polymer solutions, Journal of Non-Newtonian Fluid Mechanics, (2006) pp. 137-148, vol. 137, Elsevier.
Zahn, J.M., et al, Spinability of Respiratory Mucous, Validation of a new apparatus: The Filancemeter, Bull. Eur. Physiopath. Respir. (1986) pp. 609-613, vol. 22.

* cited by examiner

*Primary Examiner*—Daniel S Larkin
*Assistant Examiner*—Rodney T Frank
(74) *Attorney, Agent, or Firm*—Hayes Soloway PC

(57) ABSTRACT

The rheological apparatus contains a first mating surface and a second mating surface. A housing moveably orients the first mating surface to the second mating surface. A biasing member contained within the housing is connected to the first mating surface. The biasing member biases the first mating surface to move away from the second mating surface. A handle is connected to the second mating surface. The handle allows manual manipulation of the second mating surface. An extensional measurement device integral with the housing is positioned to measure a distance between the first mating surface and the second mating surface.

20 Claims, 13 Drawing Sheets

SYSTEM AND METHOD FOR MEASURING EXTENSIONAL RHEOLOGY OF BODILY FLUIDS

FIELD OF THE INVENTION

The present invention is generally related to rheological tools for analyzing viscoelasticity of bodily fluids, and more particularly is related to a system and method for measuring extensional rheology of saliva, cervical mucus, and meconium.

BACKGROUND OF THE INVENTION

Various instruments have been utilized for detecting viscoelastic properties of fluid, including adhesion, cohesion, surface tension, viscosity, and yield stress. One of the major difficulties encountered in the measurement of viscoelastic properties of fluid, other than "ideal" or Newtonian fluids, are the properties being measured may be fluctuating during measurement. For instance, it has been found that female saliva samples from the oral cavity undergo distinct in-phase physiochemical changes during the menstrual cycle.

FIG. 1 is a graph illustrating a relationship of the viscoelasticity of female sublingual saliva to blood hormones over a fourteen day period. It is known that the cervical mucus of a female has a minimum thinness or highest fluidity just before ovulation and closely coincident with the surge in estradiol and in the luteinizing hormone (LH) peak—a phenomenon that led to the development of techniques for monitoring the viscoelasticity and other properties of cervical mucus as a predictor of time of ovulation, and the improvements in rheometer or viscometer apparatus for measuring such viscoelastic properties. Though the viscoelasticity of the cervical mucus has several small dips in its characteristic curve of viscosity versus time preceding, during and following ovulation (a four-day period), there is a distinct identifiable minimum coincident with the peaking of estradiol, representing the thinning of bodily secretions. During the immediate pre-ovulatory phase, for a period of four to five days under estrogen dominance, the saliva becomes more profuse, watery, and elongatable. During the post-ovulatory phase, the saliva becomes less abundant, more viscous and less elongatable.

In healthy women with normal menstrual cycles, ovulation usually occurs between the $12^{th}$ and $14^{th}$ day prior to the next menstrual period. Specifically, the saliva is most hydrated (more than 99% watery) at the time of ovulation and is relatively dehydrated (96%-97% watery) at other times. The solid residue present after desiccation may range from 1% during ovulation to 3-4% at other times. With regards to determining time of ovulation on the basis of hormonal changes in the blood or chemical changes in the saliva, present procedures for such analysis have limited use because the results of the precise analysis are not normally available until the cycle advances. These procedures are lengthy and costly and are only adopted for unique situations.

Ovulation is defined as the moment when an ovum is released from the follicle. This knowledge led to the inventor's previous development of techniques for monitoring viscoelasticity, and other properties of saliva, as a predictor of the time of ovulation and to improvements in rheometer or viscometer apparatus for measuring viscoelastic properties (e.g., U.S. Pat. No. 4,002,056). There is a three-to-five day period at the end of which there is a distinct identifiable minimum viscoelasticity and, following ovulation, a one-to-two day period where the minimum viscoelasticity disappears.

A process for measuring the viscoelasticity of sublingual saliva is known. One device has a shape somewhat like a syringe with an outer cup, an inner cup concentric with and located within an outer cup, and a plunger. A plate attached to the end of the plunger holds a saliva sample. The plunger is inserted into the inner cup until the saliva sample is compressed against the plate in the inner cup. A predetermined amount of weight pulls the inner cup downward, stretching the saliva sample. If the viscoelasticity of the saliva is low, the saliva sample will elongate appreciably. If, the viscoelasticity of saliva is high, the saliva sample will hold the plunger and the inner cup nearly together so that the lower cup will not elongate the saliva sample indicating that ovulation will not take place in the near future.

The aforementioned viscoelasticity device is subject to flaws in that a user can improperly calibrate the device and receive an inaccurate reading. The device is also subject to sample contamination. There continues to be a need for an over-the-counter medical device that can provide females with a quick and reliable test for ovulation. Thus, a heretofore unaddressed need exists in the industry to address the aforementioned deficiencies and inadequacies.

SUMMARY OF THE INVENTION

Embodiments of the present invention provide a rheological apparatus and method for analyzing bodily fluids. Briefly described, in architecture, one embodiment of the rheological apparatus, among others, can be implemented as follows. The rheological apparatus contains a first mating surface and a second mating surface. A housing moveably orients the first mating surface to the second mating surface. A biasing member contained within the housing is connected to the first mating surface. The biasing member biases the first mating surface to pull away from the second mating surface in a substantially vertical direction. A handle is connected to the second mating surface. The handle allows manual manipulation of the second mating surface. An extensional measurement device integral with the housing is positioned to measure a distance between the first mating surface and the second mating surface.

The present invention can also be viewed as providing methods for analyzing bodily fluids with the rheological apparatus. In this regard, one embodiment of such a method, among others, can be broadly summarized by the following steps: raising a first mating surface into an extended position within a housing; depositing a sample of the bodily fluids on a second mating surface, the second mating surface connected to a handle; inserting the second mating surface with the sample into the housing; contacting the mating surfaces with the sample located therebetween; activating a biasing member contained within the housing and connected to the first mating surface, wherein activating the biasing member causes the first mating surface to move away from the second mating surface at a known rate at least until the sample fractures; and measuring the distance between the first mating surface and the second mating surface when the sample fractures, if the sample fractures, with an extensional measurement device integral with the housing.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
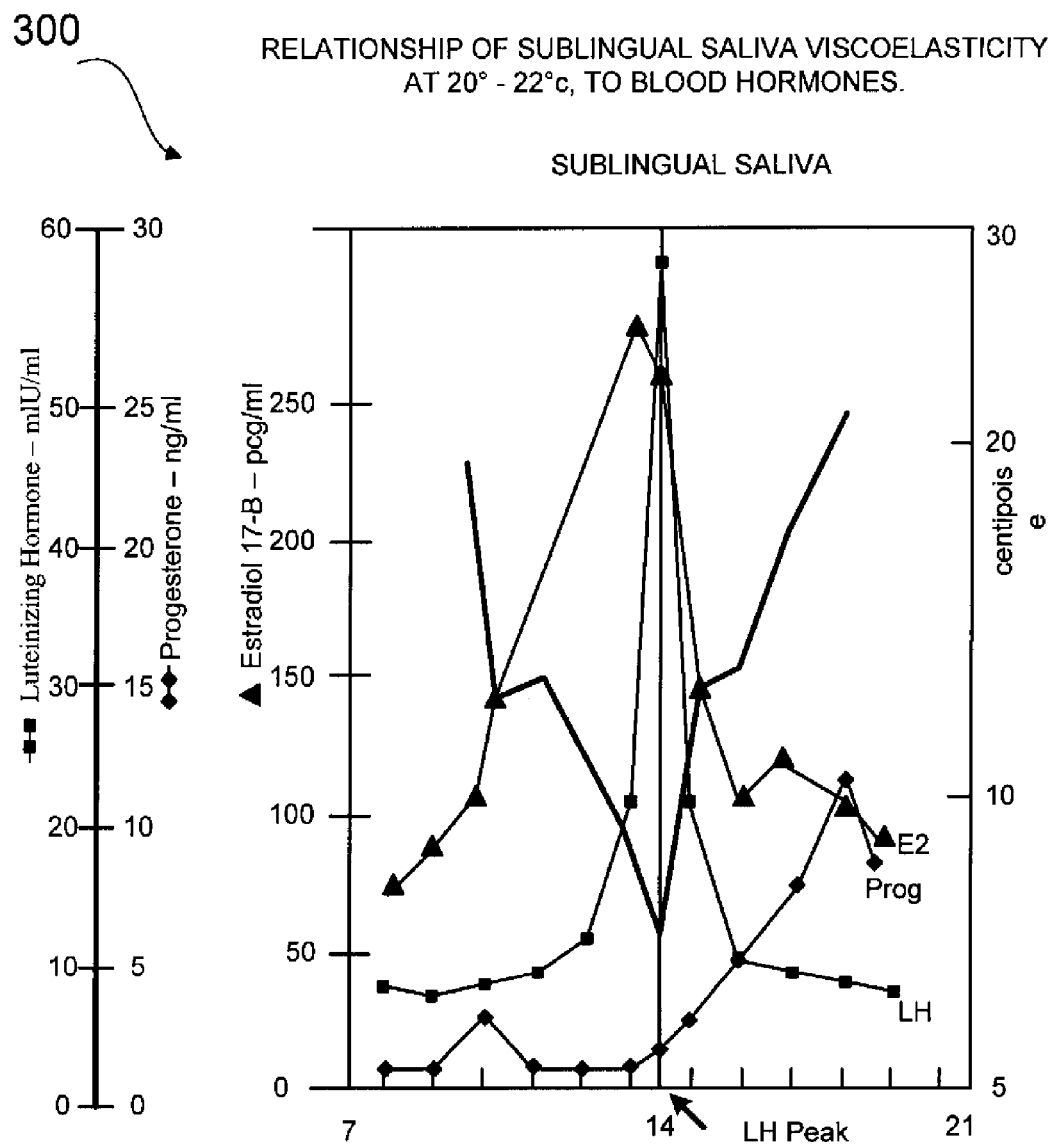
FIG. 1 is a graph illustrating a relationship of the viscoelasticity of female sublingual saliva to blood hormones over a fourteen day period.
Figure 2:
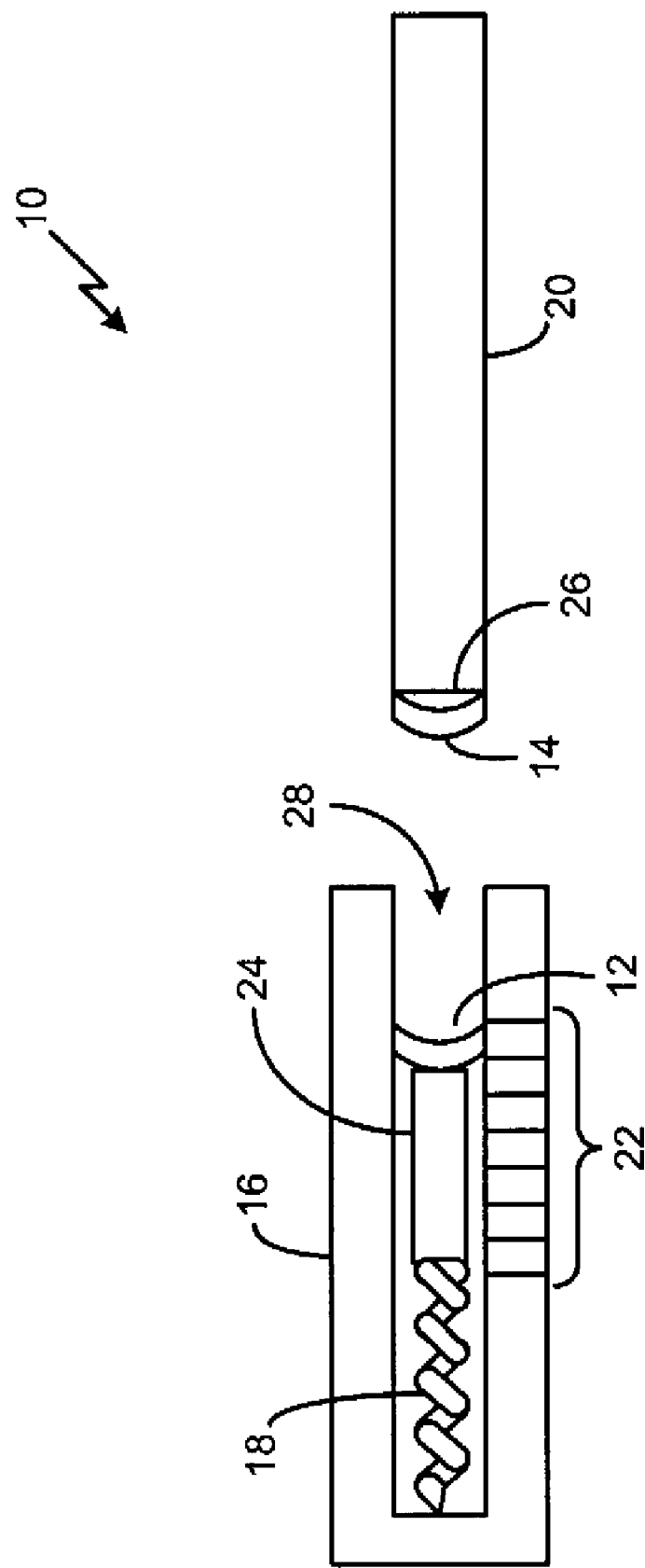
FIG. 2 is an illustration of a cross-sectional front view of a rheological apparatus, in accordance with a first exemplary embodiment of the present invention.

FIG. 2 is an illustration of a cross-sectional front view of a rheological apparatus 10, in accordance with a first exemplary embodiment of the present invention. The rheological apparatus 10 contains a first mating surface 12 and a second mating surface 14. A housing 16 moveably orients the first mating surface 12 to the second mating surface 14. A biasing member 18 contained within the housing 16 is connected to the first mating surface 12. The biasing member 18 biases the first mating surface 12 to move away from the second mating surface 14. A handle 20 is connected to the second mating surface 14. The handle 20 allows manual manipulation of the second mating surface 14. An extensional measurement device 22 integral with the housing 16 is positioned to measure a distance between the first mating surface 12 and the second mating surface 14.

In operation, as will be discussed further herein, a sample of bodily fluid, which may include, for example saliva, cervical mucus, or meconium, is captured between the mating surfaces 12, 14, which are pressed together. The mating surfaces 12, 14 are then moved apart at a known and substantially repeatable rate by the biasing member 18. As the mating surfaces 12, 14 separate, the bodily fluid sample is stretched between the mating surfaces 12, 14 until it fractures. The distance at which sublingual saliva or cervical mucus in females may fracture is relatively constant except when the female approaches ovulation and is ovulating, when the distance for fracture is materially greater. It should be noted that the reference to females herein includes women as well as animals as the rheological apparatus 10 has applications in animal husbandry. And while the phrase 'distance for fracture' is being utilized for purposes of expedience, dependent upon the length of the housing 16, the bodily fluid may not fracture when elongated in the rheological apparatus 10 during ovulation. Similarly, the distance at which meconium fractures is relatively constant for newborns except when the newborn is a carrier of cystic fibrosis, when the distance for fracture is material greater, or has cystic fibrosis, when the distance for fracture is materially greater still. The distance of fracture can be measured using the extensional measurement device 22.

As shown in the first exemplary embodiment, the mating surfaces 12, 14 may have curved mating faces. Curving the mating surfaces 12, 14 reduces an undesirable variable of surface tension between flat surfaces.

The mating surfaces 12, 14 may be disposable plates. Making the mating surfaces 12, 14 disposable allows the rest of the rheological apparatus 10 to be used repeatedly. The mating surfaces 12, 14 generally should not be used repeatedly because the mating surfaces 12, 14 become contaminated after the first use, rendering subsequent tests unreliable. More specifically, the tests may be unreliable when reusing the mating surfaces 12, 14. Those having ordinary skill in the art will recognize that some materials may be used for the mating surfaces 12, 14, which are receptive to sterilizing efforts and, thus, both reusable and disposable mating surfaces are considered to be within the scope of the present invention.

It should be noted that the cross-sectional view of the mating surfaces 12, 14 show an arcuate profile and, the mating surfaces may be at least partially spherical in dimension. The surface area of the mating surfaces 12, 14 may be at least twice the surface area offered by a flat disc filling the same circumference. The added surface area provided by the at least partially spherical shape may be useful for limiting risk of shearing of the bodily fluid from either of the mating surfaces 12, 14 while the bodily fluid is being elongated. Making the mating surfaces 12, 14 rough, also increases surface area.

For the purpose of using the mating surfaces 12, 14, the first mating surface 12 may connect to a first mounting base 24 mounted within the housing 16. Further, the first mounting base 24 may be connected to the biasing member 18 and positioned to receive the first mating surface 12. The first mating surface 12 and the first mounting base 24 may be joined by an adhesive, a hook and loop material, or any other material or substance known to those having ordinary skill in the art for temporarily securing two objects. A second mounting base 26 may be integral with the handle 20 and shaped to receive the second mating surface 14, wherein the second mating surface 14 is fixed and may be removable. As shown in the first exemplary embodiment, the second mounting base 26 and the handle 20 may be formed together. As with the first mating surface 12 and the first mounting base 24, the second mounting base 26 and the handle 20 may be joined by an adhesive, a hook and loop material, or any other material or substance known to those having ordinary skill in the art for temporarily securing two objects.

The housing 16, as shown in FIG. 2, may be a hollow, elongated sheath. The housing 16 may be, for example, a cylinder or a rectangular prism. The housing 16 may be formed from a medical grade plastic or similar substance. An opening 28 may be formed at a proximal end of the housing 16 sized to receive at least a portion of the handle 20. The second mating surface 14 may be inserted into and removed from the housing 16 through the opening 28 using the handle 20. Not shown in FIG. 2, the handle 20 may include an access opening for manually moving the first mounting base 24 and the first mating surface 12 within the housing 16.

The housing 16 includes the biasing member 18. The biasing member 18 may be, as shown in the first exemplary embodiment, a spring. The biasing member 18 may be configured to bias the first mating surface 12 away from the second mating surface 14 after the mating surfaces 12, 14 make contact. The biasing member 18 may be extended to allow the first mating surface 12 to move to the second mating surface 14 to make contact and retracted to allow the first mating surface 12 to move back from the second mating surface 14. The biasing member 18 may be another type of elastic device other than a spring and/or may include an electromagnetic, electric, or hydraulic device to separate the first mating surface 12 away from the second mating surface 14 after the mating surfaces 12, 14 make contact in a substantially smooth and repeatable manner.

The handle 20 may be made of a material similar to the material used to make the housing 16. The handle 20 is shaped to at least partially fit within the housing 16 through the opening 28. The handle 20 includes the second mounting base 26 for supporting the second mating surface 14. The handle 20 should fit far enough into the housing 16 to allow the second mating surface 14 to reach the first mating surface 12. Otherwise, the handle 20 is designed to allow a user to manually manipulate the second mating surface 14, specifically inserting it into the housing 16, without touching the second mating surface 14. The second mating surface 14, while attached to the handle 20, may be used to collect a saliva sample. The saliva sample may be collected directly from the mouth of a user by inserting the second mating surface 14 and at least a portion of the handle 20 in the mouth of the user. The handle 20 is made of a material that is non-toxic.

The extensional measurement device 22 may utilize any of a number of measurement systems known in the art. In the first exemplary embodiment, the housing 16 is a translucent material and the extensional measurement device 22 includes a number of hash marks along the housing 16 indicative of a distance. A user may visually monitor a fluid sample being stretched between the first mating surface 12 and the second mating surface 14 and, when the sample fractures, note the distance between the mating surfaces 12, 14. The extensional measurement device 22 may include one or more LEDs for visually defining distance, may include a mechanism for immobilizing the mating surfaces 12, 14 at the approximate moment the sample fractures to provide time to note the distance between the mating surfaces 12, 14, and may include an automated means of tracking the distance between the mating surfaces 12, 14 at the time of fracture.

Figure 3:
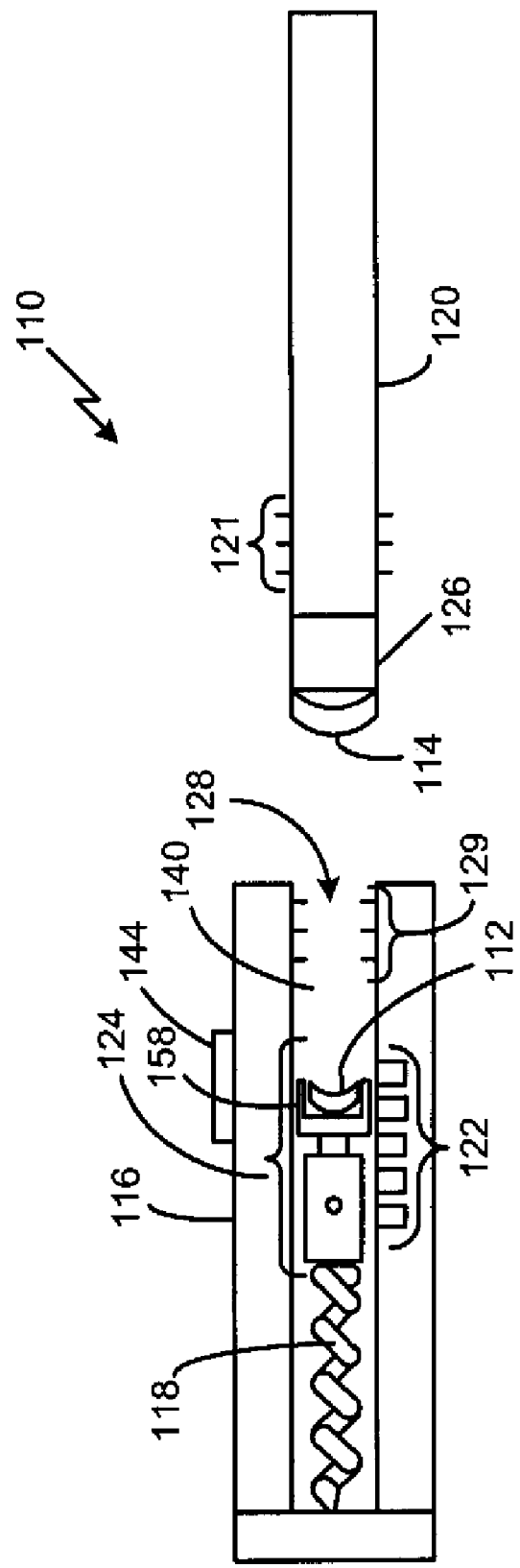
FIG. 3 is an illustration of a cross-sectional front view of a rheological apparatus, in accordance with a second exemplary embodiment of the present invention.

FIG. 3 is an illustration of a cross-sectional front view of a rheological apparatus 110, in accordance with a second exemplary embodiment of the present invention. The rheological apparatus 110 contains a first plate 112 and a second plate 114. A housing 116 moveably orients the first plate 112 to the second plate 114. A biasing member 118 contained within the housing 116 is connected to the first plate 112. The biasing member 118 biases the first plate 112 to move away from the second plate 114. A handle 120 is connected to the second plate 114. The handle 120 allows manual manipulation of the second plate 114. An extensional measurement device 122 integral with the housing 116 is positioned to measure a distance between the first plate 112 and the second plate 114.

The housing 116 is a sheath of rigid plastic shaped like a cylindrical cup with a diameter of approximately 22 to 30 millimeters and a length of 80 to 120 millimeters and an opening 128. A portion of the housing 116 proximate to the opening 128 contains a helical rib 129. A central cavity 140 is formed within the housing 116. The central cavity 140, proximate to the opening 128, may be approximately 18 millimeters in diameter. The central cavity 140 may be approximately 40 millimeters in length. The handle 120 and the housing 116 should be constructed such that when the handle 120 is inserted into the housing 116, the plates 112, 114 are properly aligned to mate effectively.

A first mounting base 124 is located within the housing 116. The first mounting base 124 reciprocates within the housing 116. Further, the first mounting base 124 may be engaged with the housing 116 to prevent the first mounting base 124 from rotating relative to the housing 116. An interior of the housing 116 may be provided with a helical groove or rib, which the first mounting base 124 rides to affect linear movement within the housing 116. An interior of the housing 116 may be provided with linear rails or grooves which the first mounting base 124 rides to prevent rotation while moving within the housing 116. Also, the central cavity 140 of the housing 116 may have a non-cylindrical shape and, more specifically, a non-circular cross-section, such that the shape of the central cavity 140 and the first mounting base 124 operate to prevent rotation within the central cavity 140. Attached to a distal end of the central cavity 140 is a coil spring, functioning, at least partially, as the biasing member 118. The coil spring retains the first mounting base 124 within the housing 116.

The handle 120 in the second exemplary embodiment, as shown in FIG. 3, may be shaped like an inverted cup, 60 to 80 millimeters long and composed of rigid plastic. A surface of the handle 120 may be ribbed 121 to engage the helical rib 129 of the housing 116. One of many possible alternatives to the complimentary ribs 121, 129 would be a friction fit arrangement between the handle 120 and the housing 116, as is known in the mechanical arts. While the complimentary ribs 121, 129 are one means of mechanically interconnecting the housing 116 and the handle 120, those having ordinary skill in the art will recognize there are many ways to mechanically removably connect to similarly shaped elements and all such connection systems are considered to be within the scope of the present invention.

Figure 4:
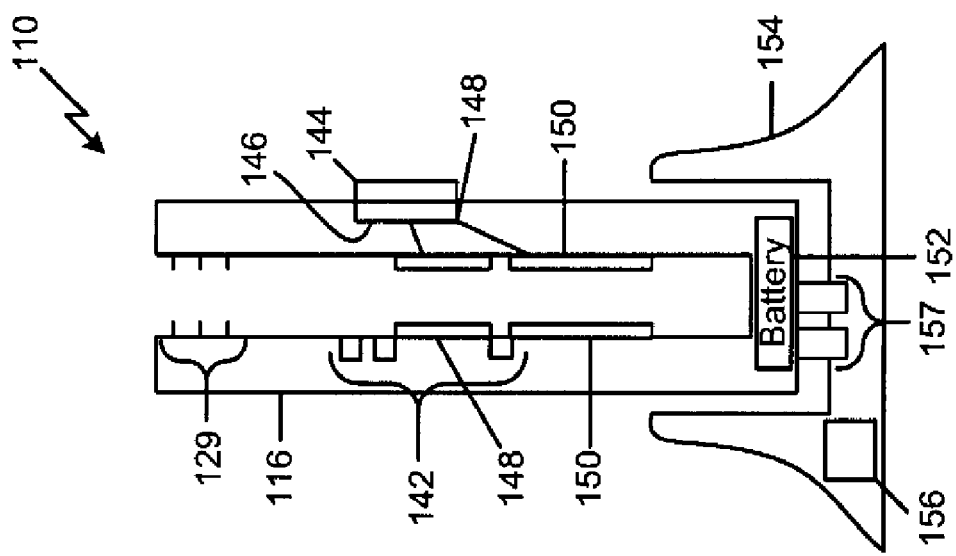
FIG. 4 is an illustration of a side view of a portion of the rheological apparatus of FIG. 3, in accordance with the second exemplary embodiment of the present invention.

FIG. 4 is an illustration of a side view of a portion of the rheological apparatus 110 of FIG. 3, in accordance with the second exemplary embodiment of the present invention. More specifically, FIG. 4 illustrates the extensional measurement device 122 according to the second exemplary embodiment of the present invention. The extensional measurement device 122 includes a plurality of LEDs 142 formed in a wall of the housing 116 to illuminate the test performed by the rheological apparatus 110. An LCD box 144 is located on an opposite side of the housing 116 from the plurality of LEDs 142 and on an exterior side of the housing 116. Within the housing 116 and in communication with the LCD box 144 is a linear measurement circuit 146 having a counter, a pair of start panels 148, a pair of stop panels 150, a battery 152. When the mating surfaces 112, 114 are substantially in contact and then move to separate, the start panels 148 signal the counter to begin. The stop panels 150 then electrically determine when the column length has fractured. The battery 152 supplies electric power to the linear measurement circuit 146. The battery 152 may be mounted within the housing 116. The LCD box 144 provides the results of the linear measurement, as communicated by the linear measurement circuit 146.

A stand 154 may be provided. The stand 154 may be integral with the housing 116 or may receive the housing 116 in a frictional fit or mechanical interconnection. The stand 154 may be up to about 100 millimeters at its widest dimension. If the stand 154 and the housing 116 are not integral, the stand 154 may have an opening substantially similar to the outer dimension of the housing 116 to snugly receive the housing 116. The stand 154 may be made of an elastomeric material. The rheological apparatus 110 may also include a memory device 156. The memory device 156 maintains at least a portion of results recorded by the linear measurement circuit 146. The memory device 156 may be stored in the housing 116 or may be stored in the stand 154. If the memory device 156 is in the stand 154, the memory device 156 may at least be in communication with the linear measurement circuit 146 when the housing 116 is connected to the stand 154 through electrical contacts 157.

Figure 5:
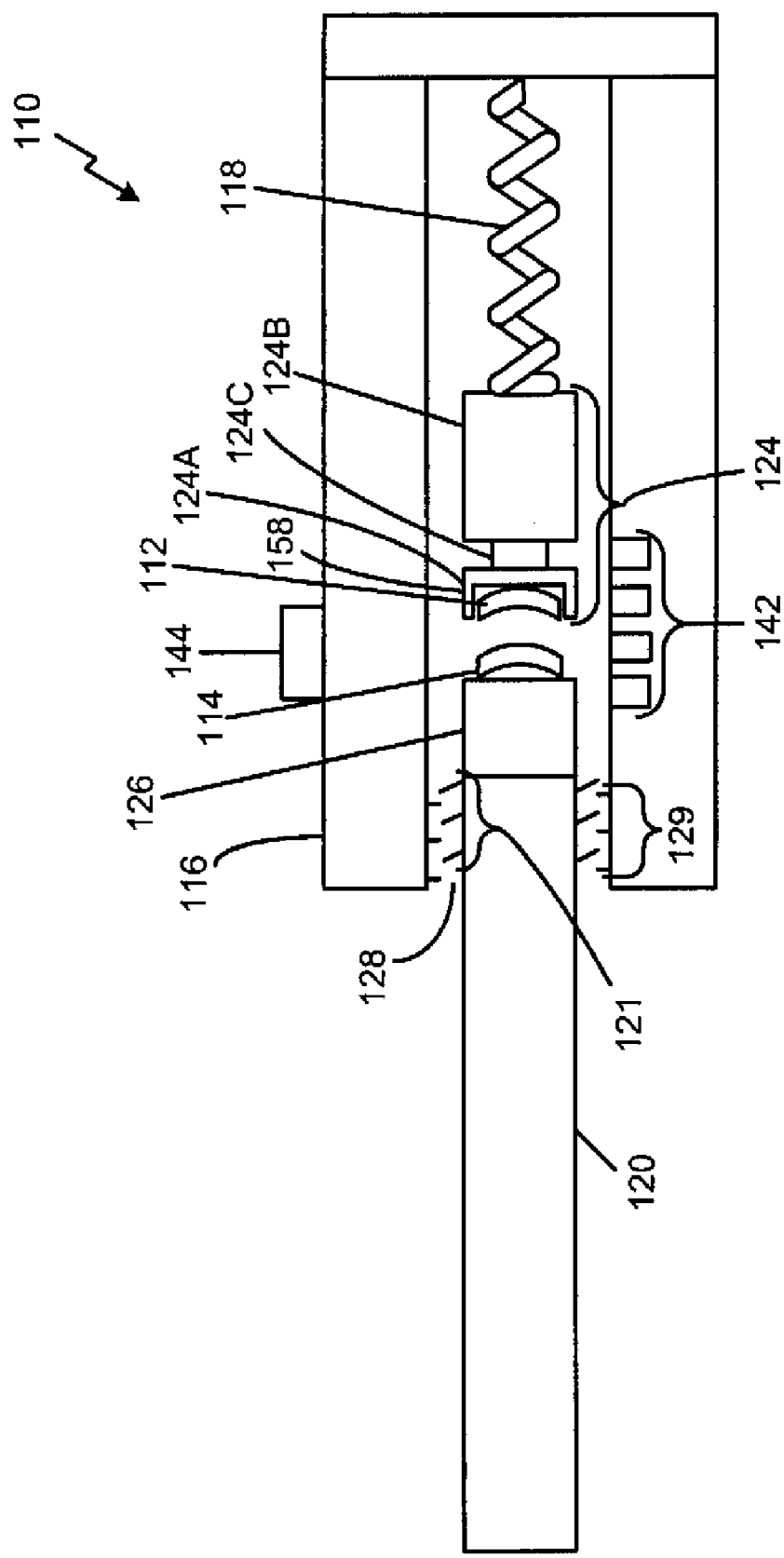
FIG. 5 is an illustration of another side view of a portion of the rheological apparatus of FIG. 3, in accordance with the second exemplary embodiment of the present invention.

FIG. 5 is an illustration of another side view of a portion of the rheological apparatus 110 of FIG. 3, in accordance with the second exemplary embodiment of the present invention. FIG. 5 shows the plates 112, 114 in contact and the housing 116 and handle 120 engaged. The first plate 112 attaches to the first mounting base 124 and the second plate 114 attaches to the second mounting base 126. The mounting bases 124, 126 are moved to allow the plates 112, 114 to have contact. The amount of force holding the plate 112, 114 and compressing the body fluid sample is related to the amount of deformation of the surface of the plates 112, 114. The amount of force between the plate 112, 114 is substantially constant and easily repeated, depending at least partly on the viscoelasticity of the substance being examined. As the biasing member 118 operates to move the plates 112, 114 apart, the plates 112, 114 remain connected by the viscoelasticity of the body fluid sample. Eventually, the force of the biasing member 118 may overcome the viscoelasticity of the body fluid sample causing the sample to fracture. If the sample separates, the electrically sensed fracturing of the sample indicates the results of the elongation of the sample on the LCD box 144.

The plates 112, 114 each have a plate surface and, when these surfaces are in contact, the area of contact is a material portion of a face of the plates 112, 114. Each face may be 0.5 to 1.5 centimeters in diameter, with a relatively roughened surface of peaks and valleys extending up to 0.02 millimeters. Factoring curvature of the plates 112, 114, the faces may have a face area of approximately 75 to 170 millimeters squared. The plates 112, 114 may be approximately 2 to 5 millimeters thick. The plates 112, 114 may be composed of a molded injection plastic.

The first plate 112 and the first mounting base 124 may be joined by an adhesive, a hook and loop material, or any other material or substance known to those having ordinary skill in the art for temporarily securing two objects. A second mounting base 126 may be integral with the handle 120 and shaped to receive the second plate 114, wherein the second plate 114 may be removable. As shown in the first exemplary embodiment, the second mounting base 126 and the handle 120 may be formed together. As with the first plate 112 and the first mounting base 124, the second mounting base 126 and the handle 120 may be joined by an adhesive, a hook and loop material, or any other material or substance known to those having ordinary skill in the art for temporarily securing two objects. The mounting bases 124, 126 may also be disposable, in which case the mounting bases 124, 126 may be provided with the plates 112, 114 integral therewith. The first mounting base 124 may include a disposable portion 124A and an integral portion 124B, wherein the integral portion 124B of the first mounting base 124 is integral with the biasing mechanism 118 and removably attaches to the disposable portion 124A of the first mounting base 124 with a fastening material 124C, such as a temporary adhesive, hook and loop material, mechanical fastener, or a comparable item as may be known in the art.

The plates 112, 114 are intended to be single use, disposable items. The plates 112, 114 can be used for only one measurement because the body fluid sample will dry in the crevices on the faces of the plates 112, 114 causing subsequent measurements to be inconsistently supported. A trough 158 may be provided about one or both of the plates 112, 114 and may be formed, at least in part, by the mounting bases 124, 126. The trough 158, preferably located about the first plate 112, may receive a run off of excess body fluid when the plates 112, 114 make contact. Allowing run off may allow the volume of body fluid tested to be more consistent across multiple tests.

A pressure applied to press the plates 112, 114 should be consistent across multiple tests for a minimum time period of approximately 2 to 4 seconds. The pressure compresses and extrudes the body fluid sample. The biasing member 118 applies a force to elongate the body fluid sample. The force used to elongate the sample may be equivalent in magnitude to the pressure applied to press the plates 112, 114 together. The force from the biasing member 118 may be approximately 0.5 to 15 grams for sublingual saliva, resulting in an extrusional stress in the range of 0-40 centistokes. Different bodily fluids will have different extrusional stress ranges that may require different biasing member 118 pressures. The extrusional stress and the length of the column resulting produces a number equivalent to the viscoelasticity of the body fluid sample, which can be used, for instance, to identify ovulation. In sublingual saliva, viscoelasticity falls over a period of 4 to 5 days until 16 to 24 hours prior to ovulation, then rises over a period of approximately 24 to 34 hours.

When taking a saliva sample, at least a portion of the handle 120 with the second plate 114 is dipped into the mouth to retrieve a sample of sublingual saliva from a saliva pool beneath the tongue. The saliva may substantially cover a face of the second plate 114. After taking the saliva sample, the end of the handle 120 bearing the second plate 114 is inserted into the opening 128 of the housing 116, which should be supported by the stand 154 (as shown in FIG. 4) with the first plate 112 elevated within the housing 116. On contact between the plates 112, 114, and commencement of the start signal, the plurality of LEDs 142 will illuminate for the elongation of the body fluid sample. If there is no elongation (substantially immediate fracture) due to a high viscoelasticity level, a separate visual signal may be provided to indicate the lack of elongation.

After the measurement of elongation is taken, the plates 112, 114 should be discarded along with any elements substantially integral with the plates 112, 114. The mounting bases 124, 126 may be discarded to maintain a clean testing environment. If the mounting bases 124, 126 are disposable, the plates 112, 114 may be provided integral with the mounting bases 124, 126. The first mounting base 124 may removably attach within the housing 116. If either of the mounting bases 124, 126 is not disposable, the plates 112, 114 may removably attach to the mounting bases 124, 126. Using disposable mounting bases 124, 126 has the benefit of allowing the plates 112, 114 to be utilized without an opportunity/requirement for fingers to touch the plates 112, 114 and contaminate the test, which would invalidate the measurement. The first mounting base 124 may be latched at the extended position, wherein the latch may be released to free the biasing member 118 to separate the plates 112, 114.

Prior to taking a sample of bodily fluid, the first plate 112 should be moved into a position to be contacted by the second plate 114. After the plates 112, 114 are installed, the second plate 114 is dipped into the mouth beneath the tongue to retrieve sublingual saliva. Preferably, the saliva covers a substantial portion on the face of the second plate 114. After taking the saliva sample, the second plate 114 and the second mounting base 126 are inserted into the opening 128 of the housing 116, preferably in a substantially smooth motion. The second mounting base 126 is releasably secured within the housing 116 with the plates 112, 114 in contact.

The start button is pressed to release the first mounting base 124, allowing the biasing member 118 to begin recoiling the first plate 112 from the second plate 114 and elongating the body fluid sample. Once the sample fractures, a measurement may be taken and stored in the memory device 156 (as shown in FIG. 4). Samples from most days will be substantially similar, establishing a base line of viscoelasticity of the user's body fluid sample. Beginning approximately 4 to 5 days prior to ovulatory peak and continuing until approximately 14 to 34 hours after ovulation, the viscoelasticity of the user's body fluid will depart from the base line and elongate to a materially greater distance prior to fracture.

Figure 6:
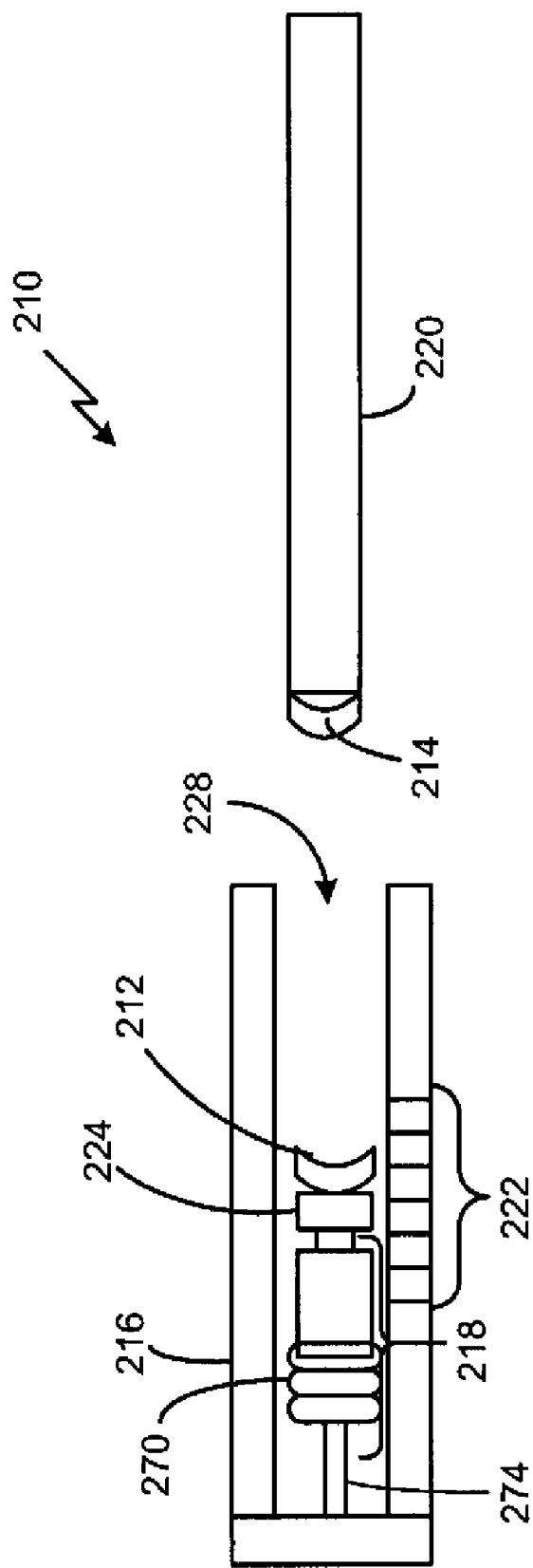
FIG. 6 is an illustration of a cross-sectional front view of a rheological apparatus, in accordance with a third exemplary embodiment of the present invention.

FIG. 6 is an illustration of a cross-sectional front view of a rheological apparatus 210, in accordance with a third exemplary embodiment of the present invention. The rheological apparatus 210 contains a first plate 212 and a second plate 214. A housing 216 moveably orients the first plate 212 to the second plate 214. A biasing member 218 contained within the housing 216 is connected to the first plate 212. The biasing member 218 biases the first plate 212 to move away from the second plate 214. A handle 220 is connected to the second plate 214. The handle 220 allows manual manipulation of the second plate 214. An extensional measurement device 222 integral with the housing 216 is positioned to measure a distance between the first plate 212 and the second plate 214.

The handle 220 should fit far enough into the housing 216 to allow the second plate 214 to reach the first plate 212. Otherwise, the handle 220 is designed to allow a user to manually manipulate the second plate 214, specifically inserting it into the housing 216, without touching the second plate 214. An opening 228 may be formed at a proximal end of the housing 216 sized to receive at least a portion of the handle 220. The second plate 214 may be inserted into and removed from the housing 216 through the opening 228 using the handle 220. The extensional measurement device 222 may utilize any of a number of measurement systems known in the art. In the third exemplary embodiment, the housing 216 is a translucent material and the extensional measurement device 222 includes a number of hash marks along the housing 216 indicative of a distance. A user may visually monitor a fluid sample being mechanically stretched between the first plate 212 and the second plate 214 and, when the sample fractures, note the distance between the plates 212, 214.

Figure 7:
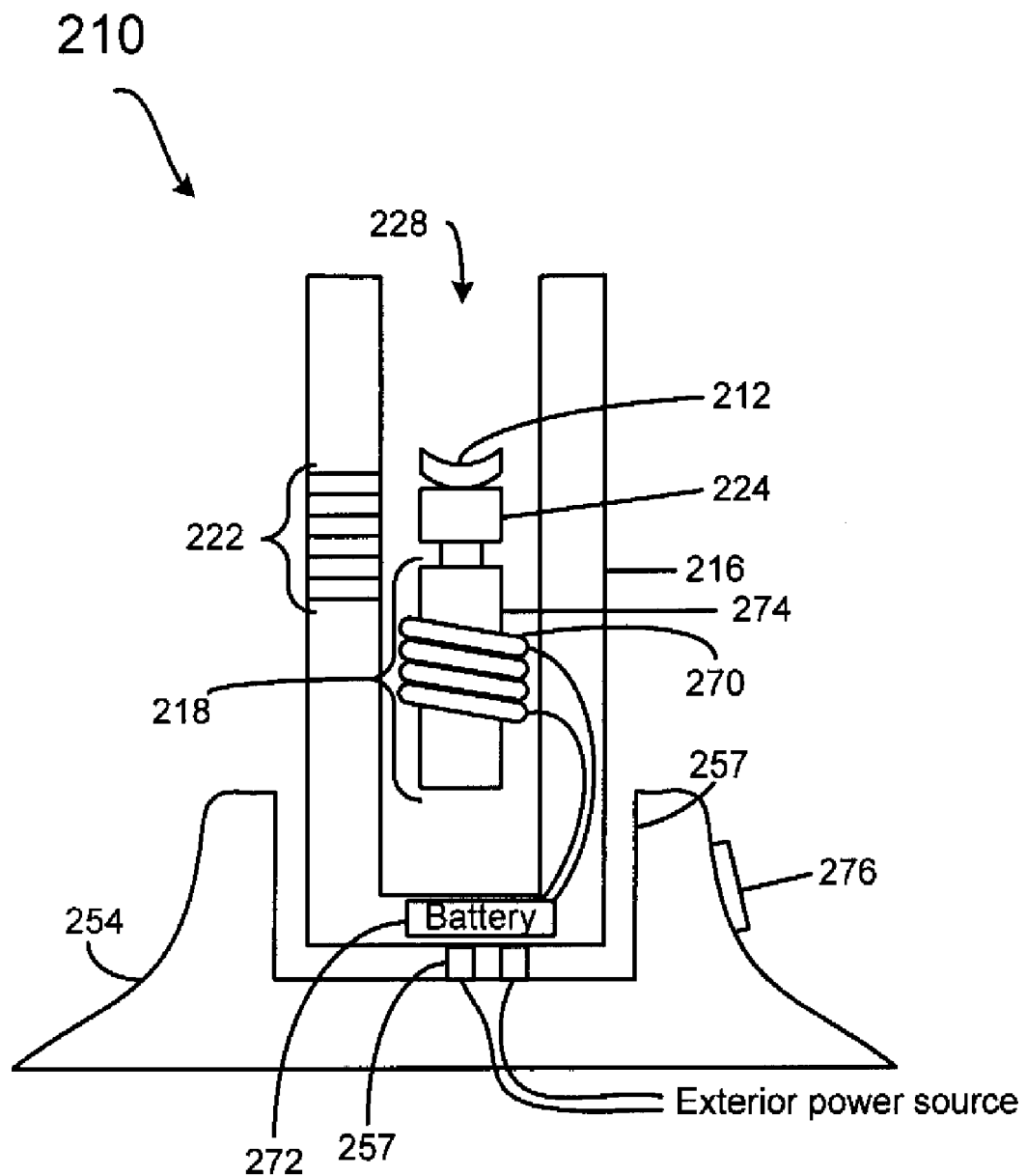
FIG. 7 is an illustration of a cross-sectional side view of an interior portion of the housing of the rheological apparatus shown in FIG. 6, in accordance with the third exemplary embodiment of the present invention.

FIG. 7 is an illustration of a cross-sectional side view of an interior portion of the housing 216 of the rheological apparatus 210 shown in FIG. 6, in accordance with the third exemplary embodiment of the present invention. In the third exemplary embodiment, the biasing member 218 may be an electromagnetic motor 270. The electromagnetic motor 270 may allow the first plate 212 to move away from the second plate 214 in a controlled manner. As shown in FIG. 7, the electromagnetic motor 270 may be connected to a power source 272, otherwise operating as is known to one having ordinary skill in the art.

The power source 272 may be located within the housing 216. The power source 272 may be a battery, as shown in FIG. 7, or a plug and cord that connects to a local outlet or other exterior power source and, further, may include an AC/DC adapter. Contacts 257 may allow electrical communication between the power source 272 and the stand 254. The electromagnetic motor 270 may be connected to a first mounting base 224 supporting the first plate 212. One or more switches 276 may be provided in communication with the power source 272 to control the current provided to the electromagnetic motor 270, which may move the electromagnetic motor 270 and first plate 212 at a constant speed along a rod 274.

Figure 8:
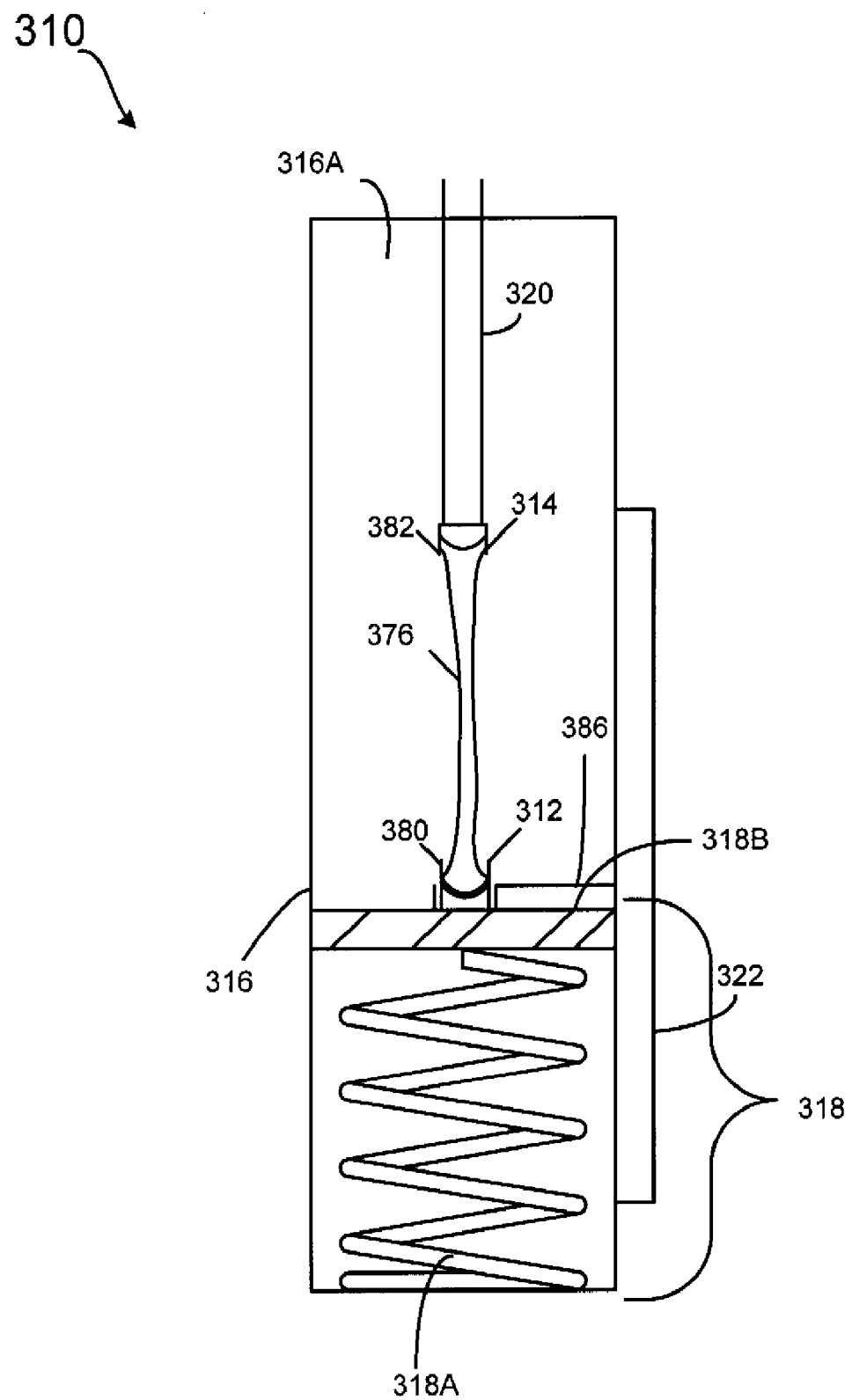
FIG. 8 is an illustration of a cross-sectional front view of a rheological apparatus, in accordance with a fourth exemplary embodiment of the present invention.

FIG. 8 is an illustration of a cross-sectional front view of a rheological apparatus 310, in accordance with a fourth exemplary embodiment of the present invention. The rheological apparatus 310 contains a first plate 312 and a second plate 314. A housing 316 moveably orients the first plate 312 to the second plate 314. A biasing member 318 contained within the housing 316 is connected to the second plate 314. The biasing member 318 biases the second plate 314 to move away from the first plate 312. A handle 320 is connected to the second plate 314. The handle 320 allows manual manipulation of the second plate 314. An extensional measurement device 322 integral with the housing 316 is positioned to measure a distance between the first plate 312 and the second plate 314.

As shown in the fourth exemplary embodiment, the biasing member 318 may include a spring 318A and a dampening seal 318B. When the plates 312, 314 are brought into contact, the spring 318A is extended. Thereafter, the apparatus 310 is released and the spring 318A retracts. The dampening seal 318B, which may be at least nearly airtight, operates to retard the retraction of the spring 318A at a set and repeatable rate. Those having ordinary skill in the art will recognize a hydraulic measure in combination with the dampening seal 318B may be utilized to retard the retraction of the spring 318A. Meanwhile, a low current may be driven through the sample 376. If the sample 376 fractures, an open circuit is created and extensional measurement device 322 determines a position of the dampening seal 318B to determine a distance the plates 312, 314 separated prior to fracture.

The rheological apparatus 310 includes a first conductive element 380 mounted at least partially about the first plate 312 and a second conductive element 382 mounted at least partially about the second plate 314. The conductive elements 380, 382 may be employed to carry a current through the sample 376. When the sample 376 is no longer able to carry the current, the sample 376 is assumed fractured and the extensional measurement device 322 takes a measurement indicative of the distance between the plates 312, 314 at the time of fracture.

As shown in FIG. 8, the extensional measurement device 322 may be mounted along a periphery of the housing 316 with a measurement arm 386 communicating a fracture of the sample 376 from the first conductive element 380 to the extensional measurement device 322. The handle 320 is inserted into the housing 316 in a reliably repeatable position to allow the plates 312, 314 to mate reliably with every measurement and to allow an electrical circuit to be formed with the second conductive element 382. While the housing 316 is shown, for illustrative purposes, to be materially wider than a width of the handle 320, the housing 316 and the handle 320 may be designed to provide a mechanically tight fit, at least along a portion of their length. Other features may be provided to provide a tight mechanical fit between the housing 316 and the handle 320 as may be understood by one with ordinary skill in the art and those features are considered to be within the scope of the present invention.

Figure 9:
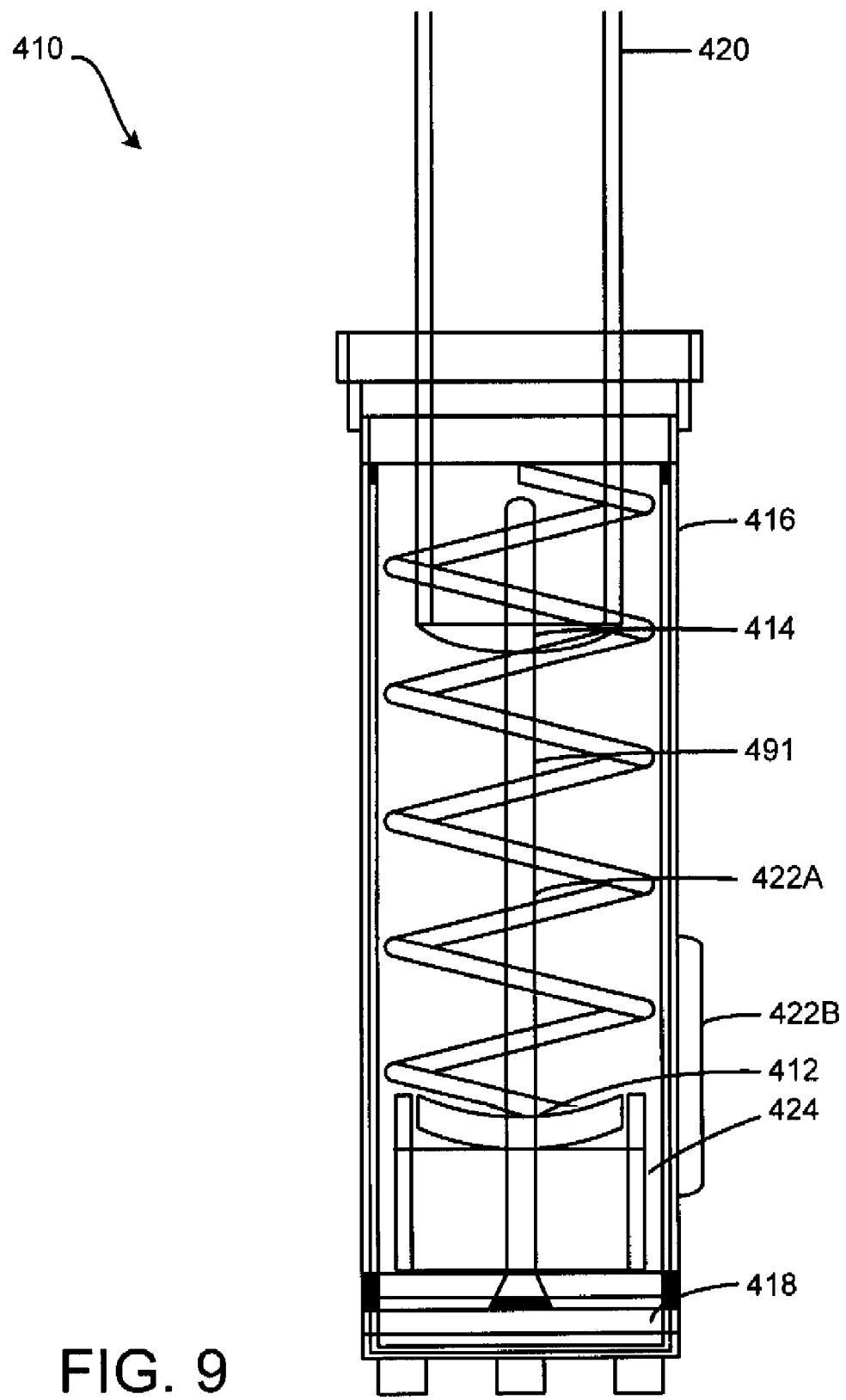
FIG. 9 is an illustration of an internal front view of a rheological apparatus, in accordance with a fifth exemplary embodiment of the present invention.

FIG. 9 is an illustration of an internal front view of a rheological apparatus 410, in accordance with a fifth exemplary embodiment of the present invention. The rheological apparatus 410 contains a first plate 412 and a second plate 414. A housing 416 moveably orients the first plate 412 to the second plate 414. A biasing member 418 contained within the housing 416 is connected to the first plate 412. The biasing member 418 is a software controlled electromagnetic motor that biases the first plate 412 to move at least away from the second plate 414. A handle 420 is connected to the second plate 414. The handle 420 allows manual manipulation of the second plate 414. An extensional measurement device 422A, 422B integral with the housing 416 is positioned to measure a distance between the first plate 412 and the second plate 414, as will be described further herein.

The handle 420 should fit far enough into the housing 416 to allow the second plate 414 to reach the first plate 412. Otherwise, the handle 420 is designed to allow a user to manually manipulate the second plate 414, specifically inserting it into the housing 416, without touching the second plate 414 to anything that would corrupt the sample. An opening 428 (shown in FIG. 10) may be formed at a proximal end of the housing 416 sized to receive at least a portion of the handle 420. The second plate 414 may be inserted into and removed from the housing 416 through the opening 428 using the handle 420. The extensional measurement device 422A, 422B may utilize any of a number of measurement systems known in the art. In the fifth exemplary embodiment, the extensional measurement device 422A, 422B includes an LED light source 422A and an LCD linear reading device 422B, as may be known to those having ordinary skill in the art. A user may visually monitor a fluid sample being mechanically stretched between the first plate 412 and the second plate 414 and, when the sample fractures, manipulate controls of the biasing mechanism 418 to stop the movement of the first plate 412. Once the first plate 412 is stopped, the LCD linear reading device 422B may provide a digital measurement of the distance between the plates 412, 414.

Figure 10:
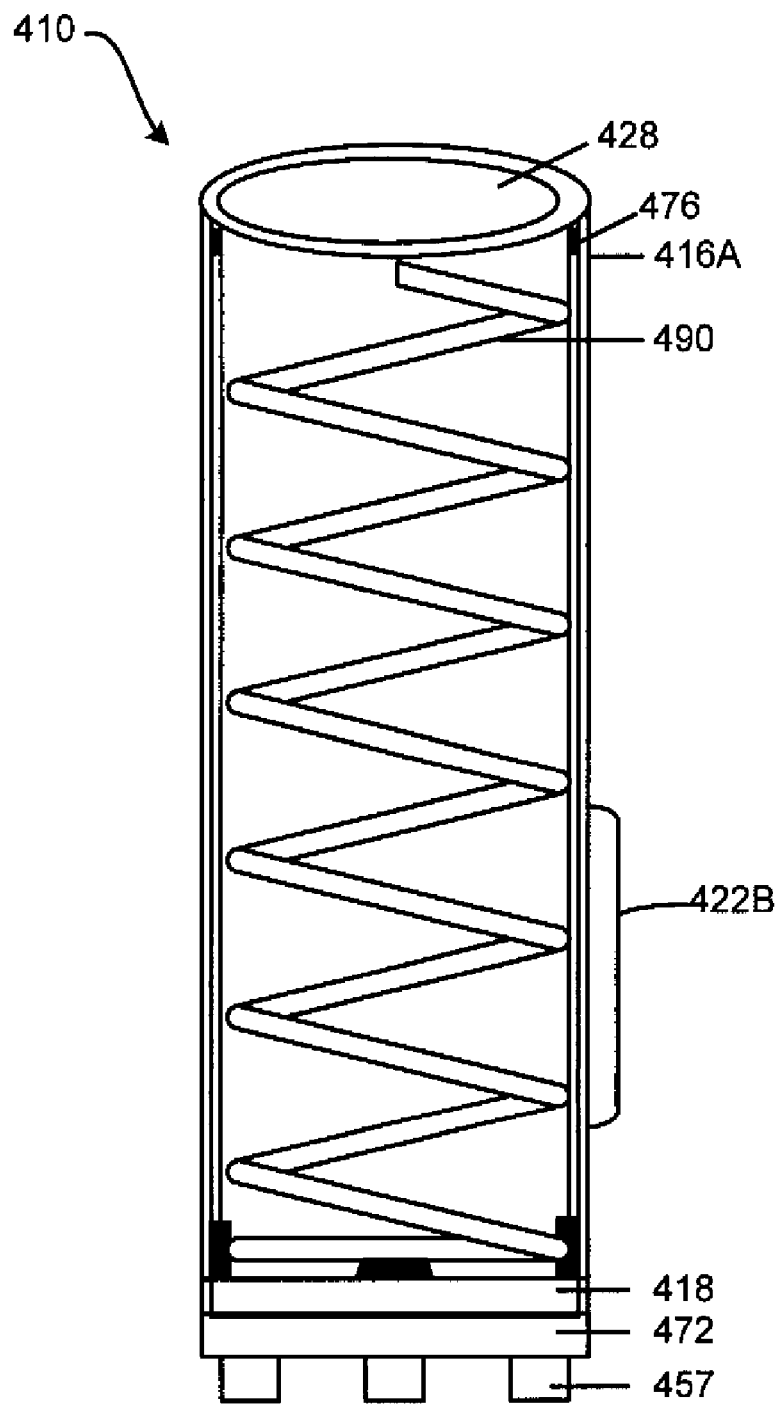
FIG. 10 is an illustration of an internal front view of a portion of the rheological apparatus shown in FIG. 9, in accordance with the fifth exemplary embodiment of the present invention.

FIG. 10 is an illustration of an internal front view of a portion of the rheological apparatus 410 shown in FIG. 9, in accordance with the fifth exemplary embodiment of the present invention. In the fifth exemplary embodiment, the biasing member 418 is an electromagnetic motor. The electromagnetic motor may allow the first plate 412 to move away from the second plate 414 in a controlled manner. As shown in FIG. 10, the biasing member 418 may be connected to a power source 472, otherwise operating as is known to one having ordinary skill in the art.

The power source 472 may be located within the housing 416. The power source 472 may be a battery, as shown in FIG. 10, or a plug and cord that connects to a local outlet or other exterior power source and, further, may include an AC/DC adapter. Contacts 457 may allow electrical communication between the power source 272 and a stand (not shown). The biasing mechanism 418 may be connected to at least one of an outer sheath 416A and an inner sheath 416B of the housing 416. The biasing mechanism 418 may rotate the outer sheath 416A relative to the inner sheath 416B to cause a first mounting base 424 supporting the first plate 412 to move vertically within the housing 416. One or more switches 476 may be provided in communication with the power source 472 to control the current provided to the biasing mechanism 418. The biasing mechanism 418 may rotate the outer sheath 416A, having at least one inner spiral groove 490, relative to an inner sheath 416B (shown in FIG. 11), causing vertical movement of the first plate 412 at a constant speed.

Figure 11:
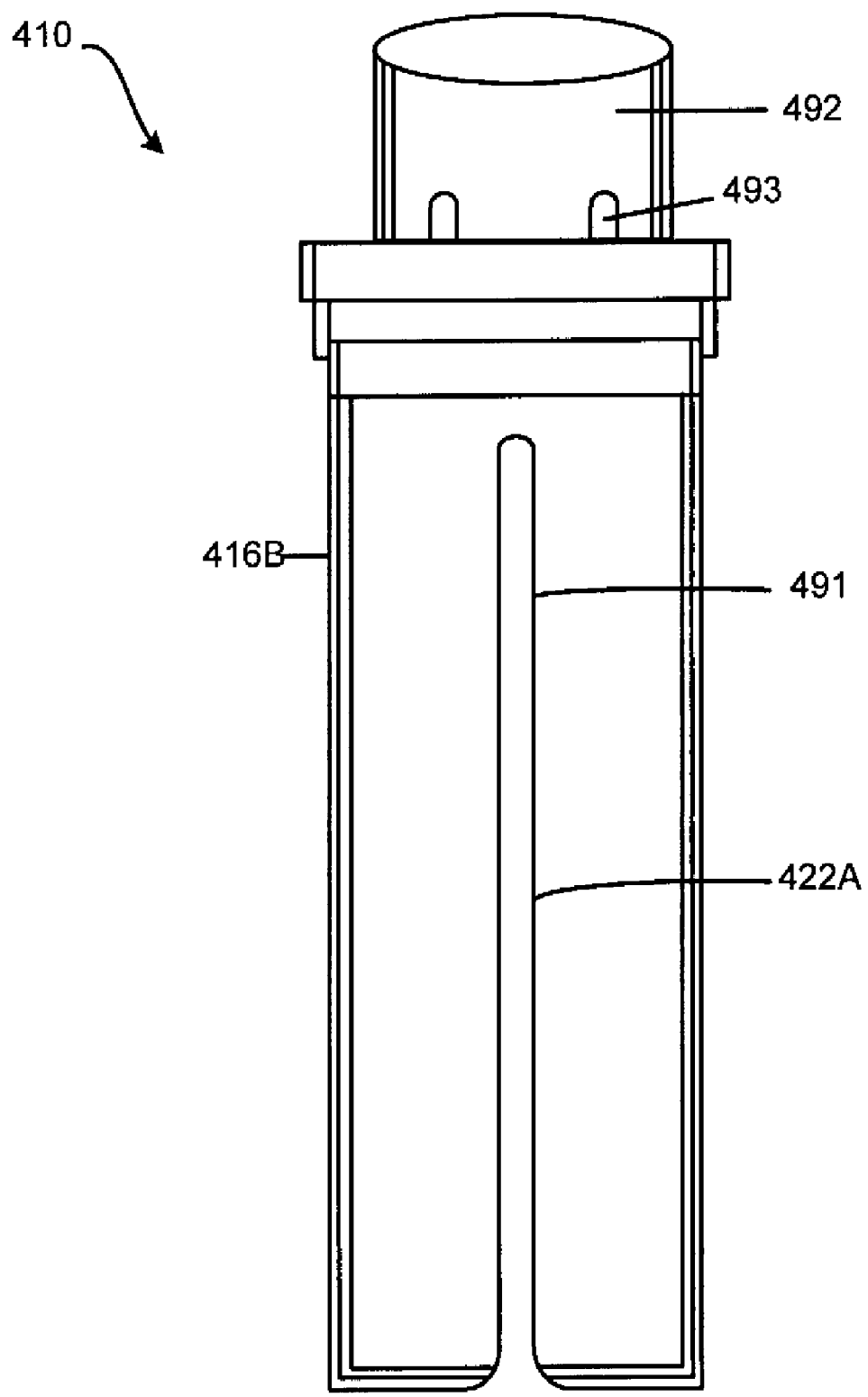
FIG. 11 is an illustration of an internal front view of a portion of the rheological apparatus shown in FIG. 9, in accordance with the fifth exemplary embodiment of the present invention.

FIG. 11 is an illustration of an internal front view of a portion of the rheological apparatus 410 shown in FIG. 9, in accordance with the fifth exemplary embodiment of the present invention. FIG. 11 shows the inner sheath 416B, which fits within the outer sheath 416A. The inner sheath 416B includes at least one vertical slot 491 that cooperates with the outer sheath 416A and a first mounting base 424 to move the mounting base 424, and the first plate 412 mounted thereon, vertically. The inner sheath 416B may also include a cap holder 492 for receiving a cap that may prevent dust and debris from entering the rheological apparatus 410 when not in use. The cap holder 492 may include a cap lock 493 or other mechanical means for interlocking with the cap to retain the cap.

Figure 12:
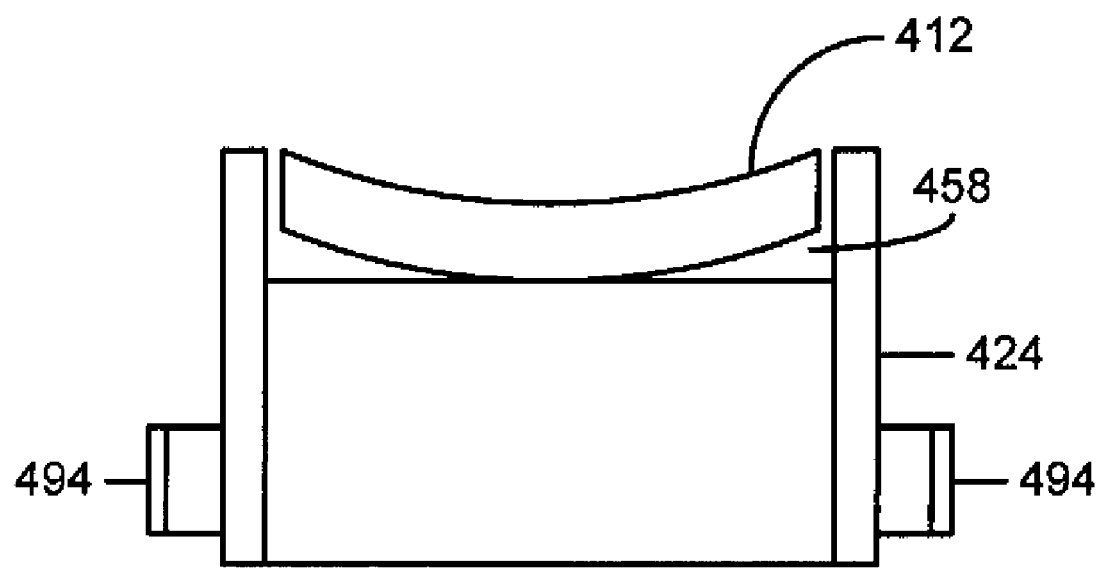
FIG. 12 is an illustration of a front view of a portion of the rheological apparatus 410 shown in FIG. 9, in accordance with the fifth exemplary embodiment of the present invention.
Figure 13:
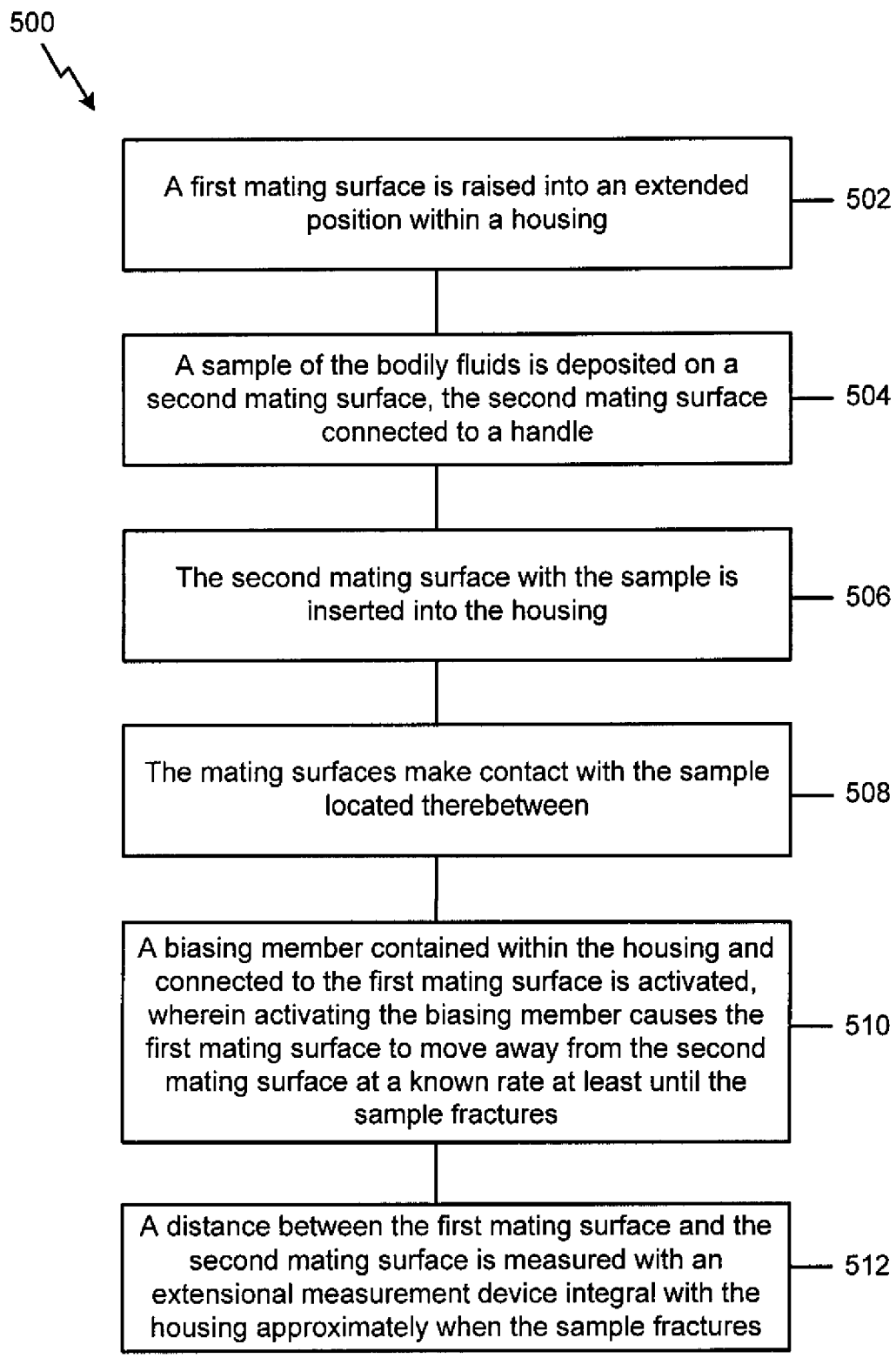
FIG. 13 is a flowchart illustrating a method of utilizing the above-mentioned rheological apparatus of FIG. 2, in accordance with the first exemplary embodiment of the invention.

FIG. 12 is an illustration of a front view of a portion of the rheological apparatus 410 shown in FIG. 9, in accordance with the fifth exemplary embodiment of the present invention. FIG. 12 includes the mounting base 424, and the first plate 412 mounted thereon. The mounting base 424 includes a pair of linear guide extensions 494. The linear guide extensions 494, when mounted within the rheological apparatus 410, traverse the vertical slots 491 (shown in FIG. 11) and set within the inner spiral grooves 490 (shown in FIG. 10). When the outer sheath 416A (shown in FIG. 10) is rotated relative to the inner sheath 416B (shown in FIG. 11), the relationship of the linear guide extensions 494, the vertical slots 491 (shown in FIG. 11) and the inner spiral grooves 490 (shown in FIG. 10) will cause the mounting base 424, and the first plate 412 mounted thereon, to move vertically. While the mounting base 424 is shown with two linear guide extensions 494, the mounting base 424 may be constructed with fewer linear guide extensions 494 or more linear guide extensions 494. Further, the linear guide extensions 494 need not all be mounted on the same plane of the mounting base 424, but may be vertically staggered. Similarly, the inner sheath 416B (shown in FIG. 11) may be constructed with fewer or greater vertical slots 491 (shown in FIG. 11) and/or the outer sheath 416A (shown in FIG. 10) may be constructed with fewer or greater inner spiral grooves 490 (shown in FIG. 10) without departing from the scope of the present invention. Also, the mounting base 424 may include a trough 458 about the first plate 412 to receive excess fluid from the sample. FIG. 13 is a flowchart 500 illustrating a method of utilizing the above-mentioned rheological apparatus 10 of FIG. 2, in accordance with the first exemplary embodiment of the invention. It should be noted that any process descriptions or blocks in flow charts should be understood as representing modules, segments, portions of code, or steps that include one or more instructions for implementing specific logical functions in the process, and alternate implementations are included within the scope of the present invention in which functions may be executed out of order from that shown or discussed, including substantially concurrently or in reverse order, depending on the functionality involved, as would be understood by those reasonably skilled in the art of the present invention.

As is shown by block 502, a first mating surface 12 is raised into an extended position within a housing 16. A sample of the bodily fluids is deposited on a second mating surface 14, the second mating surface 14 connected to a handle 20 (block 504). The second mating surface 14 with the sample is inserted into the housing 16 (block 506). The mating surfaces 12, 14 make contact with the sample located therebetween (block 508). A biasing member 18 contained within the housing 16 and connected to the first mating surface 12 is activated, wherein activating the biasing member 18 causes the first mating surface 12 to move away from the second mating surface 14 at a known rate at least until the sample fractures (block 510). A distance between the first mating surface 12 and the second mating surface 14 is measured with an extensional measurement device 22 integral with the housing 16 approximately when the sample fractures (block 512).

Sample thickness and volume is predetermined by the design configuration of the mating surfaces 12, 14, at which even slight pressure between the mating surfaces 12, 14 may cause excess fluid to be extruded into a trough 358 and a reproducible sample volume to be defined. The surface area of a fluid sample containing region is substantially equal to a combined surface area of the mating surfaces 12, 14. The rheological measurement performed when the mating surfaces 12, 14 are pulled apart at a predetermined rate relates to the yield point of the elongation of the fluid sample, among other factors.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

What is claimed is:

1. A rheological apparatus for analyzing bodily fluids, the apparatus comprising:
    a first mating surface and a second mating surface;
    a housing moveably orienting the first mating surface to the second mating surface;
    a biasing member contained within the housing and connected to at least one of the mating surfaces, wherein the biasing member biases the first mating surface and the second mating surface to move apart;
    a handle connected to the second mating surface thereby allowing manual manipulation of the second mating surface;
    an extensional measurement device integral with the housing positioned to measure a distance between the first mating surface and the second mating surface.

2. The apparatus of claim 1, wherein the first mating surface further comprises a first disposable plate and the second mating surface further comprises a second disposable plate.

3. The apparatus of claim 2, wherein the first disposable plate and the second disposable plate have complimentary curved mating faces.

4. The apparatus of claim 1, further comprising a trough formed at least partially between one of the mating surfaces and an inner surface of the housing.

5. The apparatus of claim 1, further comprising:
    a first mounting base mounted within the housing, connected to the biasing member and positioned to receive the first mating surface, wherein the first mating surface is removable; and
    a second mounting base integral with the handle and shaped to receive the second mating surface, wherein the second mating surface is removable.

6. The apparatus of claim 1, wherein the handle further comprises a trough formed at least partially about the perimeter of the second mating surface whereby excess fluid is received.

7. The apparatus of claim 1, wherein the biasing member further comprises an electromagnetic motor.

8. The apparatus of claim 1, further comprising an opening formed in the housing sized to receive at least a portion of the handle, whereby the second mating surface may be inserted into and removed from the housing.

9. The apparatus of claim 1, further comprising a cam connected to the first mating surface and manipulable from outside the housing whereby a user uses the cam to move the first mating surface within the housing.

10. A method of utilizing a rheological apparatus for analyzing bodily fluids, the method comprising the steps of:
    raising a first mating surface into an extended position within a housing;
    depositing a sample of the bodily fluids on a second mating surface, the second mating surface connected to a handle;
    inserting the second mating surface with the sample into the housing;
    contacting the mating surfaces with the sample located therebetween;
    activating a biasing member contained within the housing and connected to the first mating surface, wherein activating the biasing member causes the first mating surface to move away from the second mating surface at a known rate at least until the sample fractures or a maximum distance between the mating surfaces is achieved; and
    measuring a distance between the first mating surface and the second mating surface with an extensional measurement device integral with the housing approximately when the sample fractures, if the sample fractures.

11. The method of claim 10, wherein the first mating surface further comprises a first disposable plate and the second mating surface further comprises a second disposable plate.

12. The method of claim 11, further comprising removing and disposing of the disposable plates after the distance is measured.

13. The method of claim 10, wherein the step of contacting the mating surfaces further comprises squeezing excess bodily fluid between the mating surfaces into a trough formed at least partially between one of the mating surfaces and an inner surface of the housing.

14. The method of claim 10, further comprising removing and disposing of at least a portion of the first mounting base mounted within the housing after the distance is measured.

15. The method of claim 10, further comprising interlocking the handle and the housing.

16. The method of claim 10, wherein the step of moving the first mating surface into the extended position within the housing further comprises manually manipulating a cam integral with a first mounting base to extend the first mating surface, wherein the first mounting base supports the first mating surface.

17. The method of claim 10, further comprising standing the housing up on an end before activating the biasing member.

18. A rheological apparatus for analyzing bodily fluids, the apparatus comprising:
- a housing having an opening formed therein;
- a first mounting base moveably oriented within the housing;
- a first plate supported by the first mounting base;
- a handle interlockable with the housing;
- a second mounting base at least partially insertable through the opening and within the housing;
- a second plate supported by the second mounting base;
- a biasing member contained within the housing and connected to the first mounting base, whereby the biasing member applies a force to move the first plate away from the second mating surface; and
- an extensional measurement device integral with the housing positioned to measure a distance between the first plate and the second plate.

19. The apparatus of claim 18, further comprising a fracture sensor connected to the extensional measurement device, whereby the extensional measurement device measures the distance between the first plate and the second plate when the bodily fluid sample fractures, if the bodily fluid sample fractures.

20. The apparatus of claim 18, further comprising a memory device in communication with the extensional measurement device, whereby data representational of the measured distance is stored in the memory device.

* * * * *